(12) United States Patent
Peeters et al.

(10) Patent No.: US 11,793,172 B1
(45) Date of Patent: *Oct. 24, 2023

(54) AUTOMATED FLYING INSECT SEPARATOR

(71) Applicant: Verily Life Sciences LLC, South San Francisco, CA (US)

(72) Inventors: Eric Peeters, Redwood City, CA (US); Peter Massaro, San Carlos, CA (US); Tiantian Zha, South San Francisco, CA (US); Victor Criswell, Burlingame, CA (US); Nigel Snoad, Woodside, CA (US); Peter Smith, Pacifica, CA (US); Benjamin Krasnow, Redwood City, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/657,388

(22) Filed: Mar. 31, 2022

Related U.S. Application Data

(63) Continuation of application No. 16/360,358, filed on Mar. 21, 2019, now Pat. No. 11,291,190, which is a
(Continued)

(51) Int. Cl.
*A01K 29/00* (2006.01)
*A01K 67/033* (2006.01)
*A01K 1/03* (2006.01)

(52) U.S. Cl.
CPC ............ *A01K 29/005* (2013.01); *A01K 1/031* (2013.01); *A01K 67/033* (2013.01)

(58) Field of Classification Search
CPC ..... A01K 29/005; A01K 1/031; A01K 67/033
See application file for complete search history.

(56) References Cited

U.S. PATENT DOCUMENTS

| 3,006,320 A | 10/1961 | Bailey |
| 3,223,237 A | 12/1965 | Harrod, Jr. et al. |

(Continued)

FOREIGN PATENT DOCUMENTS

| AU | 2017339390 A1 | 4/2019 |
| CN | 1362857 A | 8/2002 |

(Continued)

OTHER PUBLICATIONS

Chinese Application No. 202210145439.8 , "Office Action", dated Jan. 20, 2023, 7 pages.
(Continued)

*Primary Examiner* — Daniel Pihulic
(74) *Attorney, Agent, or Firm* — Kilpatrick Townsend & Stockton LLP (57) ABSTRACT

An insect separating apparatus may include a sensor positioned to detect one or more insects when present within a test chamber. For example, the sensor may emit signals into the test chamber and receive reflected signals indicative of Doppler shifts caused by movement of the one or more insects. Based on information from the sensor, a computing device may determine a characteristic of the one or more insects in the chamber, such as a wing beat frequency, sex, or other characteristic. The computing device may instruct different responses based on the characteristic determined, such as activating an air mover to divert detected mosquitos out of the test chamber in response to the determined characteristics matching those of female mosquitos, or deactivating or maintaining the air mover in an inactive condition in response to the determined characteristics matching those of male mosquitos, for example, to allow passage through the chamber into a collection receptacle.

19 Claims, 6 Drawing Sheets

Related U.S. Application Data continuation of application No. 15/285,866, filed on Oct. 5, 2016, now Pat. No. 10,278,368.

(56) References Cited

U.S. PATENT DOCUMENTS

| | | |
|---|---|---|
| 3,468,289 A | 9/1969 | Broida |
| 3,750,625 A | 8/1973 | Edwards |
| 3,939,883 A | 2/1976 | Harrell et al. |
| 4,144,668 A | 3/1979 | Darncharnjitt |
| 4,212,267 A | 7/1980 | Patterson |
| 4,368,690 A | 1/1983 | Tenzer |
| 4,417,545 A | 11/1983 | Finney |
| 4,523,404 A | 6/1985 | DeYoreo |
| 4,646,683 A | 3/1987 | Maedgen, Jr. |
| 4,765,275 A | 8/1988 | Yukawa et al. |
| 4,785,764 A | 11/1988 | Muller |
| 4,863,693 A | 9/1989 | Howell |
| 5,074,247 A | 12/1991 | Gupta et al. |
| 5,178,094 A | 1/1993 | Carr et al. |
| 5,241,778 A | 9/1993 | Price |
| 5,351,643 A | 10/1994 | Hughes |
| RE35,348 E | 10/1996 | Georgi |
| 5,594,654 A | 1/1997 | Shuman et al. |
| 5,784,991 A | 7/1998 | Ukishiro et al. |
| 5,819,685 A | 10/1998 | Kappelt et al. |
| 6,244,213 B1 | 6/2001 | Tedders et al. |
| 6,293,223 B1 | 9/2001 | Blossey et al. |
| 6,474,259 B1 | 11/2002 | Gaugler |
| 6,557,487 B1 | 5/2003 | Fleischmann |
| 6,653,971 B1 | 11/2003 | Guice et al. |
| 6,688,255 B2 | 2/2004 | Donaldson et al. |
| 6,766,251 B2 | 7/2004 | Mafra-Neto et al. |
| 7,861,672 B2 | 1/2011 | Power |
| 8,322,304 B2 | 12/2012 | Chung |
| 8,733,284 B2 | 5/2014 | Courtright |
| 9,295,245 B1 | 3/2016 | Guice et al. |
| 9,510,572 B2 | 12/2016 | Aldana et al. |
| 9,594,162 B1 | 3/2017 | Sonera et al. |
| 9,642,344 B2 | 5/2017 | Unger |
| 9,992,983 B1 | 6/2018 | Sobecki et al. |
| 10,051,845 B1 | 8/2018 | Massaro et al. |
| 10,085,435 B2 | 10/2018 | Cink et al. |
| 10,159,228 B2 | 12/2018 | Hall et al. |
| 10,178,857 B2 | 1/2019 | Massaro et al. |
| 10,264,768 B2 | 4/2019 | Leo |
| 10,264,769 B2 | 4/2019 | Leo |
| 10,278,368 B1* | 5/2019 | Peeters ................. A01K 1/031 |
| 10,292,375 B1 | 5/2019 | Massaro et al. |
| 10,448,623 B1 | 10/2019 | Selby et al. |
| 10,779,521 B2 | 9/2020 | Massaro et al. |
| 10,798,924 B1 | 10/2020 | Massaro et al. |
| 11,291,190 B1* | 4/2022 | Peeters ................ A01K 67/033 |
| 2002/0035444 A1 | 3/2002 | Wilkerson et al. |
| 2002/0185605 A1 | 12/2002 | Shuman et al. |
| 2003/0188698 A1 | 10/2003 | Donaldson et al. |
| 2006/0086037 A1 | 4/2006 | Roberts |
| 2006/0196427 A1 | 9/2006 | Lepori |
| 2007/0242566 A1 | 10/2007 | Hsu |
| 2012/0017834 A1 | 1/2012 | Holland et al. |
| 2012/0306683 A1 | 12/2012 | Viikari et al. |
| 2013/0083974 A1 | 4/2013 | Tsai et al. |
| 2013/0204581 A1 | 8/2013 | Park et al. |
| 2013/0319334 A1 | 12/2013 | Newton et al. |
| 2014/0123902 A1 | 5/2014 | Kitazumi et al. |
| 2016/0066552 A1 | 3/2016 | Arsiwalla et al. |
| 2017/0142945 A1 | 5/2017 | Demetrescu et al. |
| 2017/0360014 A1 | 12/2017 | Hall et al. |
| 2018/0007874 A1 | 1/2018 | Hall et al. |
| 2018/0042211 A1 | 2/2018 | Zamboni et al. |
| 2018/0077912 A1 | 3/2018 | Comparat et al. |
| 2018/0092339 A1 | 4/2018 | Massaro et al. |
| 2018/0206464 A1 | 7/2018 | Massaro et al. |
| 2018/0206465 A1 | 7/2018 | Massaro et al. |
| 2018/0206473 A1 | 7/2018 | Massaro et al. |
| 2018/0213756 A1 | 8/2018 | Naish |
| 2018/0279598 A1 | 10/2018 | Hur et al. |
| 2018/0332817 A1 | 11/2018 | Lepek et al. |
| 2020/0260699 A1 | 8/2020 | Massaro et al. |
| 2021/0100230 A1 | 4/2021 | Metlitz et al. |
| 2021/0346913 A1 | 11/2021 | Greeley et al. |

FOREIGN PATENT DOCUMENTS

| | | |
|---|---|---|
| CN | 102415356 A | 4/2012 |
| CN | 102499182 A | 6/2012 |
| CN | 202285912 U | 7/2012 |
| CN | 203633351 U | 6/2014 |
| CN | 203735286 U | 7/2014 |
| CN | 105409893 A | 3/2016 |
| CN | 105494268 A | 4/2016 |
| CN | 109803529 A | 5/2019 |
| DE | 202018107092 U1 | 1/2019 |
| EP | 1625788 A1 | 2/2006 |
| EP | 3522702 A1 | 8/2019 |
| GB | 2349786 A | 11/2000 |
| KR | 20040087696 A | 10/2004 |
| KR | 20090002991 A | 1/2009 |
| KR | 101805742 B1 | 12/2017 |
| SG | 11201902973 S | 5/2019 |
| WO | 2010038055 A1 | 4/2010 |
| WO | 2012115959 A2 | 8/2012 |
| WO | 2015111007 A1 | 7/2015 |
| WO | 2015126855 A1 | 8/2015 |
| WO | 2016024164 A1 | 2/2016 |
| WO | 2016079089 A1 | 5/2016 |
| WO | 2016153339 A1 | 9/2016 |
| WO | 2018067376 | 4/2018 |
| WO | 2019116744 A1 | 6/2019 |

OTHER PUBLICATIONS

European Application No. 21194896.3, "Intention to Grant", dated Jan. 10, 2023, 8 pages.

U.S. Appl. No. 15/285,623, Notice of Allowance, dated Apr. 16, 2018, 9 pages.

U.S. Appl. No. 15/285,624, Final Office Action, dated May 6, 2019, 10 pages.

U.S. Appl. No. 15/285,624, Final Office Action, dated Jul. 2, 2020, 9 pages.

U.S. Appl. No. 15/285,624, Non-Final Office Action, dated Jan. 14, 2019, 10 pages.

U.S. Appl. No. 15/285,624, Non-Final Office Action, dated Apr. 9, 2020, 8 pages.

U.S. Appl. No. 15/285,642, Non-Final Office Action, dated Aug. 9, 2018, 5 pages.

U.S. Appl. No. 15/285,642, Notice of Allowance, dated Jan. 23, 2019, 7 pages.

U.S. Appl. No. 15/285,866, Notice of Allowance, dated Dec. 31, 2018, 7 pages.

U.S. Appl. No. 15/285,866, "Supplemental Notice of Allowability", dated Jan. 10, 2019, 2 pages.

U.S. Appl. No. 15/286,059, Advisory Action, dated Jul. 2, 2020, 2 pages.

U.S. Appl. No. 15/286,059, Final Office Action, dated Apr. 16, 2020, 31 pages.

U.S. Appl. No. 15/286,059, Non-Final Office Action, dated Nov. 22, 2019, 25 pages.

U.S. Appl. No. 15/286,059, Non-Final Office Action, dated Sep. 3, 2020, 29 pages.

U.S. Appl. No. 15/716,981, Notice of Allowance, dated May 5, 2020, 5 pages.

U.S. Appl. No. 15/716,981, Notice of Allowance, dated Jan. 28, 2020, 9 pages.

U.S. Appl. No. 16/055,253, Non-Final Office Action, dated Sep. 21, 2018, 6 pages.

U.S. Appl. No. 16/055,253, Notice of Allowance, dated Jan. 10, 2019, 5 pages.

U.S. Appl. No. 16/360,358, Non-Final Office Action, dated Aug. 6, 2021, 5 pages.

(56) References Cited

OTHER PUBLICATIONS

U.S. Appl. No. 16/360,358, Notice of Allowance, dated Nov. 29, 2021, 5 pages.
U.S. Appl. No. 16/396,970, Notice of Allowance, dated Jun. 4, 2020, 5 pages.
U.S. Appl. No. 16/396,970, Notice of Allowance, dated Feb. 26, 2020, 8 pages.
U.S. Appl. No. 16/593,210, Non-Final Office Action, dated Mar. 29, 2022, 27 pages.
U.S. Appl. No. 16/856,881, Notice of Allowance, dated Mar. 9, 2022, 10 pages.
U.S. Appl. No. 16/856,881, Notice of Allowance, dated Jun. 29, 2022, 5 pages.
AU2017339390, "First Examination Report", dated Oct. 15, 2021, 3 pages.
Balestrino et al., "A New Larval Tray and Rack System for Improved Mosquito Mass Rearing", Journal of Medical Entomology, vol. 49, No. 3, May 2012, pp. 595-605.
Carvalho et al., "Mass Production of Genetically Modified Aedes Aegypti for Field Releases in Brazil", Journal of Visualized Experiments, vol. 83, Jan. 2014, pp. 1-10.
Application No. CN201780062207.3, Notice of Decision to Grant, dated Dec. 28, 2021, 3 pages.
Application No. CN201780062207.3, Office Action, dated Apr. 6, 2021, 6 pages.
Application No. EP17858927.1, Extended European Search Report, dated Apr. 24, 2020, 7 pages.
Application No. EP17858927.1, Notice of Decision to Grant, dated Oct. 7, 2021, 2 pages.
Application No. EP21194896.3, Extended European Search Report, dated Dec. 7, 2021, 10 pages.
Liu et al., "A Review of Recent Sensing Technologies to Detect Invertebrates on Crops", Precision Agriculture, vol. 18, Issue 4, Aug. 31, 2016, pp. 1-37.
Nebuloni et al., "Doppler Radar Signatures of Migrating Birds", Poster Session 5, New or Alternative Concepts & Methods, Available Online at: https://ams.confex.com/ams/pdfpapers/21432.pdf and https://ams.confex.com/ams/30radar/techprogram/paper_21432.htm, Jul. 20, 2001, 3 pages.
Application No. PCT/US2017/054094, International Preliminary Report on Patentability, dated Apr. 18, 2019, 10 pages.
Application No. PCT/US2017/054094, International Search Report and Written Opinion, dated Nov. 29, 2017, 12 pages.
Application No. SG11201902973S, Notice of Decision to Grant, dated May 25, 2022, 6 pages.
Application No. SG11201902973S, Written Opinion, dated Nov. 30, 2020, 7 pages.

* cited by examiner

FIG. 14

AUTOMATED FLYING INSECT SEPARATOR

CROSS-REFERENCE TO RELATED APPLICATION

This application is a continuation of U.S. patent application Ser. No. 16/360,358, filed Mar. 21, 2019, which is a continuation of U.S. patent application Ser. No. 15/285,866, filed Oct. 5, 2016, titled "Automated Flying Insect Separator," which are incorporated herein by reference in their entireties.

TECHNICAL FIELD

The present disclosure generally relates to separating insects based on automatically-identified characteristics of the insects, and more specifically, but not necessarily limited to, separating male mosquitos from female mosquitos based on information obtained from mosquitos flying within range of provided sensors.

BACKGROUND

Various methods of insect population control exist. One particular method, generally referred to as the "sterile insect technique," includes introducing large numbers of sterile male insects into an insect population. As a result, female insects in the population may be more likely to mate with sterile males and thus are less likely to produce offspring. This reduction in the number of offspring may result in the population ultimately being eliminated or otherwise being brought down to acceptable levels.

SUMMARY

Various examples of the present disclosure are directed to automatically determining insect characteristics based on information from sensors and using that determination to physically separate the insects into different groups.

In one example, an insect separating apparatus can be provided that includes a first receptacle sized for insect receiving, a second receptacle sized for insect receiving, and a test chamber defining a test volume. A first enclosed path connecting the test volume to the first receptacle can also be included along with a second enclosed path connecting the test volume to the second receptacle. The apparatus can also include a Doppler sensor, an air mover, and a computing device. The Doppler sensor can include a signal emitter and a signal receiver. The emitter can be configured to output a signal into the test volume, and the receiver can be configured to receive a reflection of the signal. The air mover can be selectively operable to move air toward the first enclosed path in response to an activation signal. The computing device can include a processor and a non-transitory computer-readable medium comprising processor-executable instructions to cause the processor to receive sensor information from the Doppler sensor, determine whether the received sensor information corresponds to a Doppler shift indicative of at least one female insect being present in the test volume, and cause the activation signal to be sent to the air mover in response to the received sensor information corresponding to a Doppler shift indicative of at least one female insect being present in the test volume.

In another example, a method includes receiving sensor information about an insect located within a chamber. The sensor information can include information indicative of a Doppler shift caused by movement of the insect. The method can also include determining a characteristic of the insect based at least in part on the Doppler shift. The method can also include selectively activating an air mover based on the characteristic determined.

In a further example, a system includes a test chamber. The test chamber has a boundary surface defining a test volume within the test chamber. An entry is formed in the boundary surface of the test chamber and sized for insect receiving into the test volume. A first exit is formed in the boundary surface of the test chamber and sized for insect passage out of the test volume. A second exit is formed in the boundary surface of the test chamber and sized for insect passage out of the test volume. The system can also include a sensor, a separator, and a computing device. The sensor can be positioned relative to the test volume for obtaining sensor information about an insect received into the test volume through the entry. The separator can be selectively operable to facilitate movement of the insect from the test volume toward the first exit, or facilitate movement of the insect from the test volume toward the second exit. The computing device can include a processor and a non-transitory computer-readable medium comprising processor-executable instructions to cause the processor to perform certain actions. The processor can receive the sensor information from the sensor, determine a characteristic of the insect received into the test volume based at least in part on the sensor information received, and determine whether the characteristic matches stored criteria. The processor may provide first instructions to the separator in response to determining that the characteristic matches the stored criteria. The first instructions can be configured to cause the separator to facilitate movement of the insect from the test volume toward the first exit. The processor may provide second instructions to the separator in response to determining that the characteristic does not match the stored criteria. The second instructions may be configured to cause the separator to facilitate movement of the insect from the test volume toward the second exit.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of systems for separating insects based on an automatically determined characteristic of an insect. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a mosquito breeding program seeks to control or reduce a wild mosquito population by releasing sterile male mosquitos to breed with wild female mosquitos. To obtain mosquitos for such releases, the breeding program rears mosquitos from eggs laid in captivity. Once the mosquitos have matured into adults, the program separates the male and female mosquitos into different containers so that the male mosquitos can be released into the wild. To accomplish this separation, the breeding program employs a system that allows adult mosquitos to fly from a rearing container through a chamber, where a sensor observes the mosquitos. Specifically, the sensor projects a sound wave into the chamber at particular frequency and registers the frequency of echoes returning from bouncing off of the mosquitos. A computer processes the differences between the projected sound waves and the echoes to determine whether any mosquitos flying through the chamber are beating their wings as slow as female mosquitos, which typically beat their wings slower than male mosquitos during flight. If the computer determines that any wingbeats are as slow as female mosquitos, the computer triggers a pressurized air hose to blast air through the chamber to push all mosquitos in the chamber into a reject container. Otherwise, if the computer determines that no wingbeats are as slow as female mosquitos, the computer prevents the pressurized air hose from blasting, and the mosquitos in the chamber (presumably all males) are allowed to fly out of the chamber into a separate collection container. Over time, the separate collection container can accumulate a quantity of male insects that is sufficiently large and free of female insects for effective use in the sterile insect technique.

Figure 1:
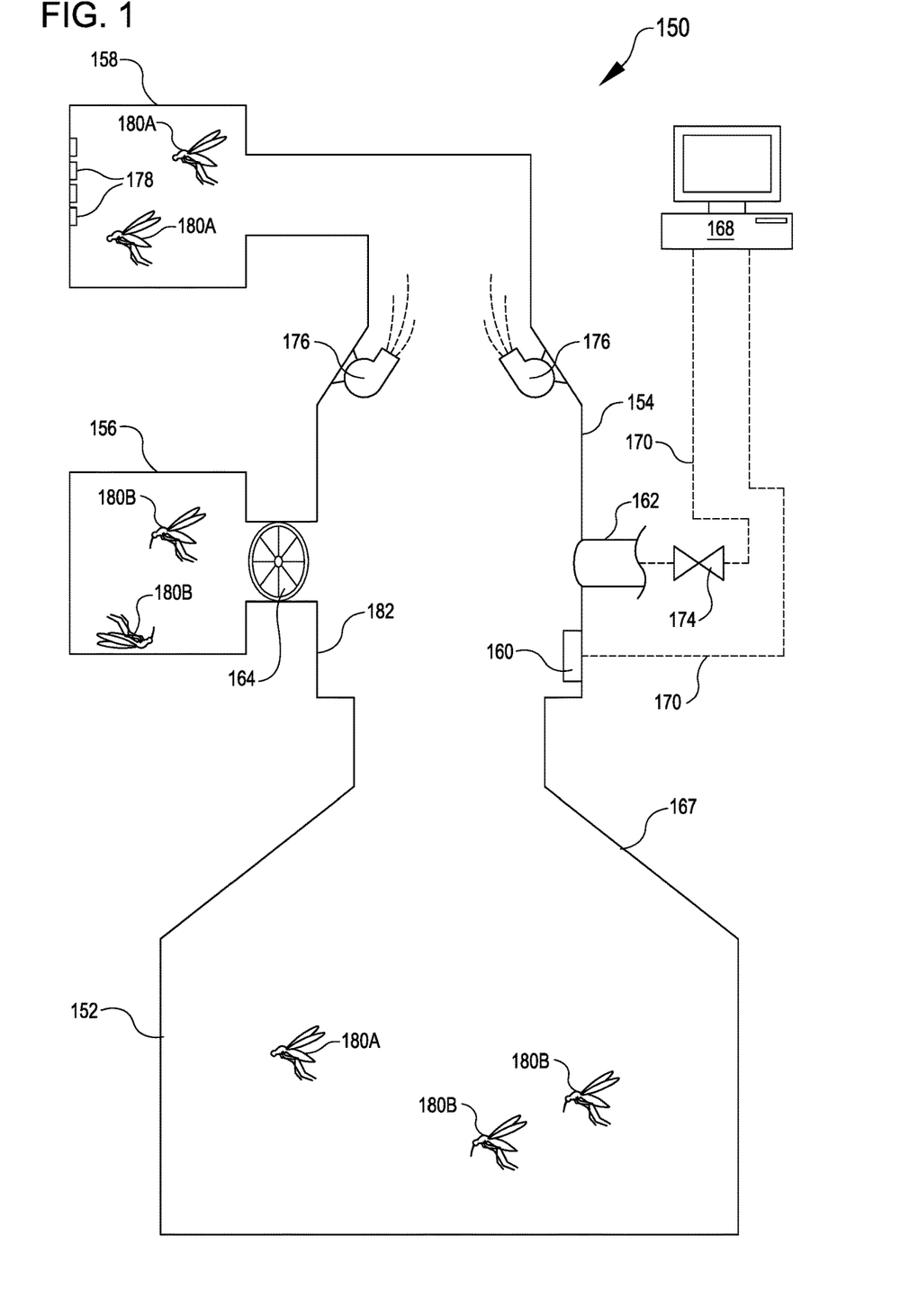
FIG. 1 shows an illustrative example of a system for separating insects into different groups based on an automatically detected characteristic.

FIG. 1 illustrates a system 150 for separating or sorting a first type of insect 180A (e.g., male mosquitos) from a second type of insect 180B (e.g., female mosquitos) according to certain examples. Although description of the system 150 herein will primarily refer to mosquitos for simplicity, the system 150 could also be applied to other forms of insects, including, but not limited to, fruit-flies, codling moths, screw-worms, honeybees, Africanized honeybees, house flies, or wasps.

The system 150 shown in FIG. 1 includes an origination chamber 152, a test volume or test chamber 154, a diverted chamber 156, and a pass-through chamber 158. The test chamber 154 may have an entry from the origination chamber 152 and respective exit paths connecting respectively to the diverted chamber 156 and the pass-through chamber 158. Generally, insects 180 (individually labeled either as male insects 180A or female insects 180B) arriving in the test chamber 154 from the origination chamber 152 may be either diverted to the diverted chamber 156 as a first receptacle or allowed to reach the pass-through chamber 158 as a second receptacle. This may effectively sort the insects 180 in a useful manner, such as populating the pass-through chamber 158 with a large quantity of male mosquitos 180A that is sufficiently free of female mosquitos 180B to be effective for use in the sterile insect technique.

The test chamber 154 shown in FIG. 1 is outfitted with a sensor package 160, a pressurized air input 162, and a one-way valve 164. The sensor package 160 may include an appropriate sensor or combination of sensors for detecting the presence and/or characteristics of insects 180 that reach the test chamber 154 from the origination chamber 152 through a funnel 167 or other suitable transition structure.

The air mover 162 may be a part of an airflow system that can be controlled to facilitate movement of any insects 180 toward one of the exits of the test chamber 154. For example, the air mover 162 correspond to a pressurized air hose, a fan, a venturi, a source of vacuum pressure or other suction, or some other structure that individually or in combination can provide airflow for evacuating any insects 180 from the test chamber 154 into the diverted chamber 156, e.g., through the one-way valve 164. Although the air mover 162 is shown in FIG. 1 as a pressurized air hose located outside of and across from the diverted chamber 156 for providing air movement to push insects into the diverted chamber 156, other location or component options are possible, including, but not limited to, a suction apparatus arranged to provide air movement to pull insects into the chamber 156. Additionally, although the system 100 is shown in FIG. 1 with the air mover 162, the system 100 may additionally, or alternatively, use other separator or sorter components, such as a movable solid barrier to push or pull insects into the diverted chamber 156, or devices capable of selectively terminating insects from the test chamber 154 (e.g., swatters, lasers, gassers, or other elements that may supply insect-lethal doses of heat, pressure, water, chemical agents, etc.).

The one-way valve 164 may allow passage of insects 180 into the diverted chamber 156 from the test chamber 154 in response to air pressure from the air mover 162 and otherwise prevent or impede passage of insects 180 from the diverted chamber 156 back to the test chamber 154. For example, the one-way valve 164 is shown in FIG. 1 as a revolving door with panels that may block passage when not rotating toward the diverted chamber 156 in response to air pressure from the air mover 162. Other options for the one-way valve 164 include, but are not limited to, biased flaps, spring-loaded tapered structures, ball-check valves, diaphragm check valves, swing check valves, stop-check valves, lift-check valves, in-line check valves, duckbill valves, or other forms of check valve. In some examples, the one-way valve 164 may include a butterfly valve (or other variety of valve that may be toggled by an external action that is not dependent on airflow from the air mover 162) that may be selectively operated (e.g., by the computer system 168 described below) to open for passage of air from the airflow system.

The sensor package 160 and/or other elements of system 150 may be coupled with a computer system 168 by a communication link 170, which may correspond to one or more suitable wired or wireless connections by which elements may communicate with each other individually or in combination. For example, the sensor package 160 may provide information via the communication link 170 to the computer system 168. Based on the information from the sensor package 160, the computer system 168 may provide control signals via the communication link 170 to an air mover controller 174 for controlling the air mover 162. The air mover controller 174 may be any structure capable of changing a state of the air mover 162. For example, the air mover controller 174 may correspond to a valve on a pressurized hose or a switch for a fan. The air mover controller 174 may respond to an activation signal from the computer 168 to activate the air mover 162 to introduce a blast of air for pushing any insects 180 from the test chamber 154 into the diverted chamber 156. Alternatively, the computer 168 may send signals to the air mover controller 174 to deactivate the air mover 162 or maintain the air mover 162 in an inactive or deactivated condition to instead permit an insect 180 to continue flying through the test chamber 154 to reach the pass-through chamber 158.

In some aspects, the system 150 may include additional features to encourage an insect 180 to fly in a useful path through the system 150. For example, fans 176, pumps, or other such pressure-affecting devices may be included to provide a mild vacuum or other airflow pattern that encourages insects 180 to fly toward the pass-through chamber 158. As another example, an attractant 178 (e.g., a sound, light, heat and/or chemical lure) may be placed in the pass-through chamber 158. In some examples, an electrostatic charge coating or other surface treatment 182 may be applied to walls of the test chamber 154 and/or at other places in the system 150 to discourage an insect 180 from landing so that the insect 180 is more likely to remain in flying motion for movement through the system 150.

The sensor package 160 may include any of a variety of suitable sensors. Examples may include, but are not limited to, sound sensors, light sensors, heat sensors, humidity sensors, and optical sensors. Sensors in the sensor package 160 may be used individually or in combination to provide information about conditions in the test chamber 154. In some examples, data from one sensor may be used to improve accuracy of analysis conducted based at least in part on data from another sensor. For example, temperature and/or humidity sensors may provide information about conditions of air in the chamber that may affect a speed of sound in the chamber and corresponding assessment of readings from an ultrasonic sensor.

Figure 1A:
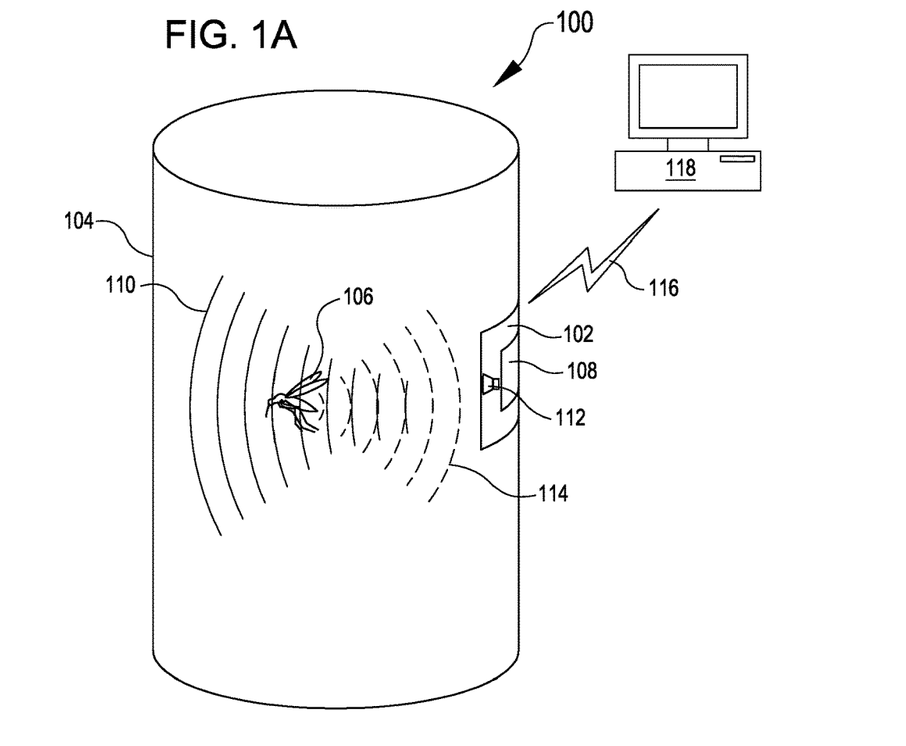
FIG. 1A shows an illustrative example of a system for determining a characteristic of an insect using Doppler ultrasound.

One example system 100 for determining a characteristic of an insect using Doppler ultrasound is shown in FIG. 1A. The system 100 includes a control unit 102 positioned within a tube 104. The control unit 102 may correspond to a portion of the sensor package 160 described above. An insect 106 may pass through the tube 104 and by the control unit 102. The insect 106 may be, but is not limited to, a mosquito, a honeybee, an Africanized honeybee, a house fly, or a wasp. The control unit 102 may house a sensor, for example, a transceiver 108. The transceiver 108 may be capable of transmitting and receiving signals. In some examples, however, a separate transmitter and/or a separate receiver may be substituted for all or part of the transceiver 108. The transceiver 108 can generate an output signal 110 over a period of time. The transceiver 108 may generate the output signal 110 in any suitable medium. For example, the transceiver 108 may correspond to an ultrasonic transceiver, and the output signal 110 can be transmitted through an acoustic transmitter 112 (e.g., a piezoelectric transducer) as sound waves. Other examples of suitable mediums for the output signal 110 may include light (e.g., laser) and radar. Although such alternatives are possible, for the sake of simplicity, description herein will focus on sound waves as a medium, and in particular those in the ultrasonic range. Accordingly, hereinafter, the transceiver 108 may be referred to as the ultrasonic transceiver 108. The output signal 110 from the ultrasonic transceiver 108 can be an ultrasonic signal having a particular frequency. The output signal 110 can reflect off the body and wings of the insect 106 and return to the ultrasonic transceiver 108 as a reflected signal 114. The reflected signal 114 can be received by the ultrasonic transceiver 108 over a period of time. The ultrasonic transceiver 108 may be positioned to transmit across at least a portion of the test volume.

The reflected signal 114 can have a frequency that is different from the frequency of the output signal 110 depending on the insect. The difference between the frequency of the output signal 110 and the reflected signal 114 can correspond to the direction of the insect wing's movement as the output signal 110 reflects off the insect wing. For example, the frequency of the reflected signal 114 can be greater than the frequency of the output signal 110 when the output signal 110 reflects off an insect wing that is moving towards the ultrasonic transceiver 108. The frequency of the reflected signal 114 can be less than the frequency of the output signal 110 when the output signal 110 reflects off an insect wing that is moving away from the ultrasonic transceiver 108. The increase or decrease in the frequency of the reflected signal 114 as compared to the output signal 110 can be due to the insect wing moving towards the ultrasonic transceiver 108 or away from the ultrasonic transceiver 108, and is known as the Doppler effect or Doppler shift. The difference between the frequency of the output signal 110 and the reflected signal 114 (e.g., the measured Doppler shift) can be used to determine the wing velocity and/or wing beat frequency of the insect.

The system 100 can include a communication link 116 that communicatively couples the control unit 102 to a computing device 118. The computing device 118 can be located away from the control unit 102. The control unit 102 can transmit a signal to the computing device 118 via the communication link 116 that corresponds to the reflected signal 114. The computing device 118 can determine a characteristic about the insect 106 based on difference between the output signal 110 and the reflected signal 114, for example, using one or more algorithms and/or machine learning (e.g., neural networks). In some examples, the control unit 102 may include a computing device that may determine a characteristic about the insect 106.

While the system 100 in the example shown in FIG. 1A is used with respect to a tube, in other examples, it can be positioned in a variety of settings. In one example, the system 100 could be positioned in, or proximate to, a bee hive to monitor the insect activity in and/or proximate to the hive. The system 100 may determine if Africanized honey bees, wasps, or other invasive species have threatened the hive. In another example, the system 100 can be positioned in, or proximate to, a vessel that receives adult mosquitoes (e.g., a tube as described above). The vessel could be part of a device used in sterile insect breeding programs to separate male and female mosquitos. In another example, the system 100 can be positioned in, or proximate to, a vessel that receives insects in the natural environment. The system 100 could monitor the species of insects in the vicinity of the system 100, and in some examples, the system 100 could monitor the sex of the insects in the vicinity of the system 100.

Figure 2A:
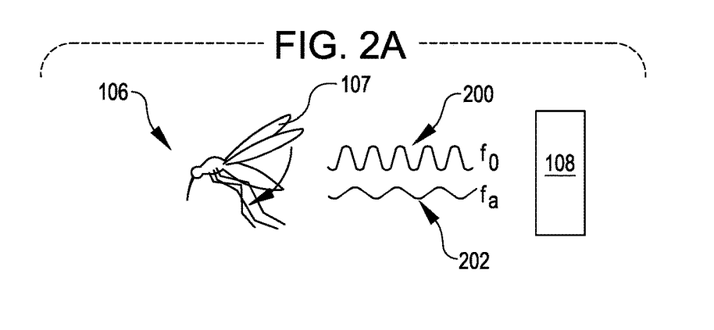
FIGS. 2A-2B shows an illustrative example of an output signal, transmitted by an element of the system of FIG. 1, reflecting off the wing of an insect, according to an example of the present disclosure.
Figure 2B:
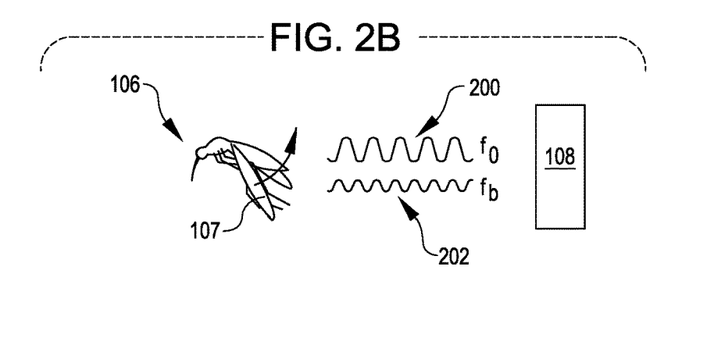

FIG. 2A shows an illustrative example of an output signal 200 reflecting off the wing 107 of the insect 106, shown as reflected signal 202, when the wing 107 is moving away from the ultrasonic transceiver 108. The output signal 200 can have a frequency $f_o$. In some examples, the frequency $f_o$ of the output signal 200 may be in a range between 20,000 hertz (Hz) and 100,000 Hz. The reflected signal 202 can have a frequency $f_a$. The frequency $f_a$ of the reflected signal 202 can be less than the frequency $f_o$ of the output signal 200 as the wing 107 moves away from the ultrasonic transceiver 108. FIG. 2B shows an illustrative example of the output signal 200 reflecting off the wing 107 of the insect 106, shown as reflected signal 202, when the wing 107 is moving toward the ultrasonic transceiver 108. The output signal 200 has a frequency $f_o$ and the reflected signal 202 has a frequency $f_b$. The frequency $f_b$ of the reflected signal 202 can be greater than the frequency $f_o$ of the output signal 200 as the wing 107 moves towards the ultrasonic transceiver 108. Thus, as an illustrative example, if the frequency $f_o$ of the output signal 200 is 25,000 Hz, the frequency $f_a$ of the reflected signal 202 when the wing 107 is moving away may be 24,000 Hz, while the frequency $f_b$ of the reflected signal 202 when the wing 107 is moving toward the ultrasonic transceiver 108 may be 26,000 Hz. The change in frequency between the output signal 200 and the reflected signal 202 (e.g., whether the reflected signal 202 registers above or below the output signal 200) can reflect the direction of motion of the wing 107 of the insect 106. This information can be used to determine the wing beat frequency of the insect 106. The wing beat frequency of the insect 106 is the number of complete cycles of wing beats per second.

Figure 3:
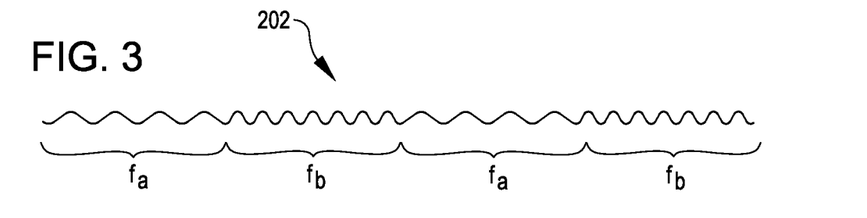
FIG. 3 shows an illustrative example of a reflected signal, received by an element of the system of FIG. 1, corresponding to one wing beat of an insect, according to an example of the present disclosure.

FIG. 3 shows an illustrative example of a change in frequency of an ultrasound signal through one complete cycle of the movement of the wing 107 of the insect 106 as it flies. As can be seen, the change in frequency can correspond to the wing 107 moving away from the ultrasonic transceiver 108 (reflected signal 202 having frequency $f_a$), the wing 107 moving toward the ultrasonic transceiver 108 (reflected signal 202 having frequency $f_b$), the wing 107 again moving away from the ultrasonic transceiver 108 (reflected signal 202 having frequency $f_a$), and again the wing 107 moving toward the ultrasonic transceiver 108 (reflected signal 202 having frequency $f_b$). The number of complete cycles per second, as shown in FIG. 3, is approximately the wing beat frequency of the insect 106. Different insects may have different wing beat frequencies. For example, a female *Culex stigmatosoma* mosquito may have an average wing beat frequency of about 350 Hz, a male *Culex tarsalis* mosquito may have an average wing beat frequency of about 550 Hz, a house fly may have an average wing beat frequency of about 200 Hz, a midge may have an average wing beat frequency of about 1,000 Hz, and a honey bee may have an average wing beat frequency of about 150-200 Hz. By determining the wing beat frequency of the insect 106, the species of the insect 106 may be determined. Male and female insects of the same species also may have different wing beat frequencies. For example, a female *Aedes aegypti* mosquito may have an average wing beat frequency of about 484 Hz while a male *Aedes aegypti* mosquito may have an average wing beat frequency of about 715 Hz.

Figure 4A:
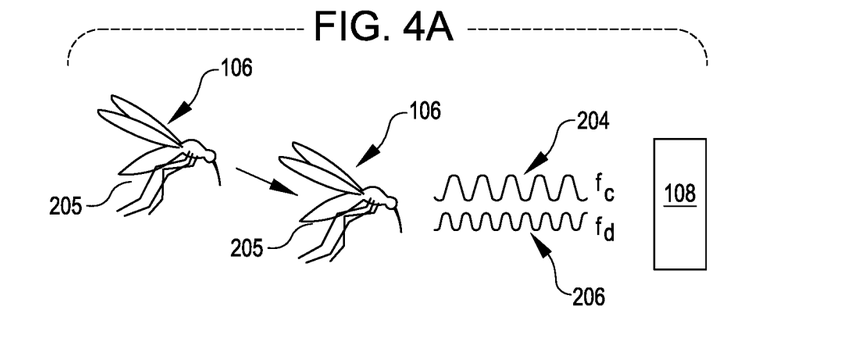
FIGS. 4A-4B show an illustrative example of an output signal, transmitted by an element of the system of FIG. 1, reflecting off a body of an insect, according to an example of the present disclosure.
Figure 4B:
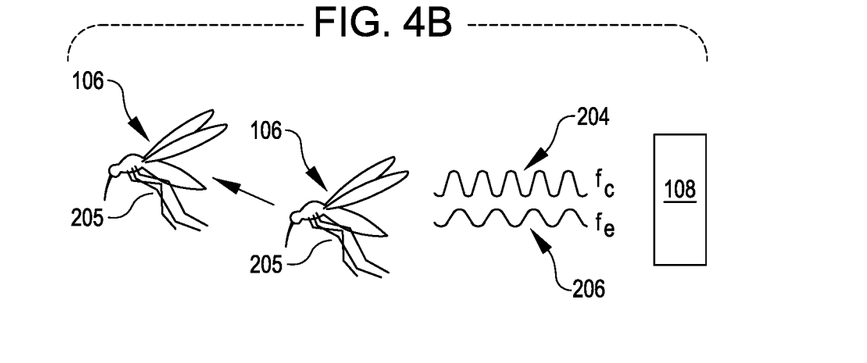

In some examples, as shown in FIGS. 4A-4B, an output signal 204 having a frequency $f_c$ transmitted by the ultrasonic transceiver 108 can reflect off the body 205 of the insect 106, shown as reflected signal 206. As shown in FIG. 4A, if the insect 106 moves towards the ultrasonic transceiver 108, the reflected signal 206 can have a frequency $f_d$ that is greater than the frequency $f_c$ the output signal 200. As shown in FIG. 4B, if the insect 106 moves away from the ultrasonic transceiver 108, the reflected signal 206 can have a frequency $f_e$ that is less than the frequency $f_c$ the output signal 200. The difference between the frequency of the reflected signal 206 and the output signal 200 can be used to determine at what speed the insect 106 is flying. Changes in the speed of a detected insect 106 may be used to determine a flight pattern of the insect. The flight speed and/or flight pattern of the insect 106 can be used to determine the species of the insect 106. For example, insects 106 of different species may be distinguished from one another based on different top or typical speeds of each species. As another example, the reflected signal 206 from the body 205 of the insect 106 may be used to determine whether the insect 106 is circling rather than flying in a steady direction. Such information may be useful for distinguishing between different species that have a similar wing beat frequency but different circling behavior. In some aspects, the flight speed of the insect 106 can also be used in determining the sex of the insect 106. A female mosquito may generally fly faster than a male mosquito for certain species, for example. As described further below, in some aspects, both the frequency shift of an output signal reflecting off an insect's wings and the frequency shift of an output signal reflecting off an insect's body can be used to determine the species and/or sex of the insect.

In some aspects, amplitude differences may be used to determine information about an insect 106. For example, in some aspects, a reflected signal 202 from a wing 107 of an insect 106 (e.g., FIG. 2A or 2B) and a reflected signal 206 from a body 205 of an insect 106 (e.g., FIG. 4A or 4B) may both occur in response to a signal emitted from the ultrasonic transceiver 108 (e.g., the output signal 200 in FIGS. 2A and 2B may be the same as the output signal 204 in FIGS. 4A and 4B). The reflected signal 202 from the wing 107 and the reflected signal 206 from the body 205 may have different amplitudes that may be used to differentiate between the sources. For example, the reflected signal 206 from the body 205 may have an amplitude that is smaller than the amplitude of the output signal 204, and the reflected signal 202 from the wing 107 may have an amplitude that is smaller than the reduced amplitude of the reflected signal 206 from the body 205. In some aspects, comparing the relative amplitudes of the reflected signal 202 from the wing 107 and the reflected signal 206 from the body 205 may provide information about the size of the wing 107 relative to the size of the body 205 of an insect 106. Such information may be used to determine a species and/or sex of the insect 106. In some aspects, distinguishing between the reflected signal 202 from the wing 107 and the reflected signal 206 from the body 205 may facilitate filtering or other signal processing techniques that may improve a confidence in determinations being made and/or that may increase the number of details that can be determined.

Figure 5:
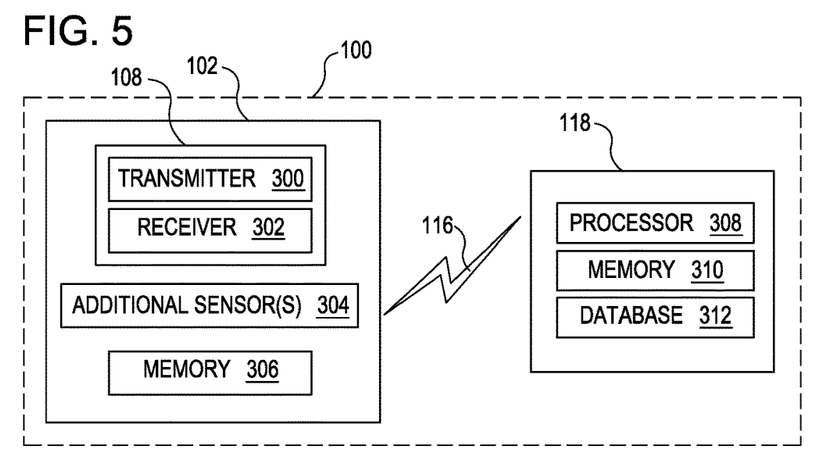
FIG. 5 shows a block diagram of an illustrative example of the system of FIG. 1, according to an example of the present disclosure.

FIG. 5 shows a block diagram of an illustrative example of the system 100 of FIG. 1A, including the control unit 102 and the computing device 118. The ultrasonic transceiver 108 may include a transmitter 300 and a receiver 302. The transmitter 300 can generate the output signal 110 (shown in FIG. 1A), and the receiver 302 can receive the reflected signal 114 (shown in FIG. 1A).

In some examples, the control unit 102 can also include one or more additional sensors 304 for gathering additional data regarding the surrounding environment. In some examples, the additional sensor 304 may be a temperature sensor or a humidity sensor. The control unit 102 may also include memory 306. Memory 306 can store data corresponding to the output signal 110 (shown in FIG. 1A), the reflected signal 114 (shown in FIG. 1A), and other data gathered by the additional sensor 304.

The data gathered by the additional sensor 304 may be transmitted to the computing device 118 via the communication link 116. In some aspects, the communication link 116 may be a wireless communication link and may include wireless interfaces, such as IEEE 802.11, BlueTooth™, radio frequency identification (RFID), near-field communication (NFC), or radio interfaces for accessing cellular telephone networks (e.g., transceiver/antenna for accessing a CDMA, GSM, UMTS, or other mobile communications network). In some aspects, the communication link 116 may be a wired communication link and may include interfaces, such as Ethernet, USB, IEEE 1394, fiber optic interface, voltage signal line, or current signal line. The control unit 102 can transmit data to the computing device 118 via the communication link 116. In some examples, the control unit 102 may transmit data corresponding to the output signal 110, the reflected signal 114, data gathered by the additional sensor 304, in addition to other data (e.g., age of the insect and time of day).

The computing device 118 of the system 100 can include a processor 308, memory 310, and a database 312. In some aspects, one or more of the elements of the computing device 118 may be located away from the computing device 118. For example, the database 312 may be located on a separate computing device or server. The processor 308 can determine one or more characteristics of the insect 106 (shown in FIG. 1A) based on the data transmitted by the control unit 102. In some examples, the processor 308 can determine characteristics of the insect 106 based on the output signal 110 and the reflected signal 114 received from the control unit 102. In some aspects, the processor 308 may determine characteristics of the insect 106 based on the output signal 110, the reflected signal 114, as well as additional data, for example, but not limited to, temperature data, humidity data, time of day, data indicating the age of the insect, or other types of data.

In some examples the processor 308 may determine one or more characteristics of the insect 106 including for example, but not limited to, the wing beat frequency of the insect 106, the speed of the insect 106, the species of the insect 106, and/or the sex of the insect 106. For example, the processor 308 may determine the species of the insect 106 based on one or more of the wing beat frequency of the insect 106, the speed of the insect 106, the size of the insect 106, the age of the insect 106, and/or additional data. In some examples, the processor 308 may determine the sex of the insect 106 based on one or more of the wing beat frequency of the insect 106, the speed of the insect 106, the size of the insect 106, the age of the insect 106, and additional data. The additional data may be received from the control unit 102 or other sources. The additional data may be data stored in the database 312 and may include, but is not limited to, data related to the known wing beat frequency of various species of insects, the known size of various species of insects, the known speed of various species of insects, the known wing beat frequency of male and female insects of the same species, the known size of male and female species of insects, the known speed of male and female insects of the same species.

Figure 6:
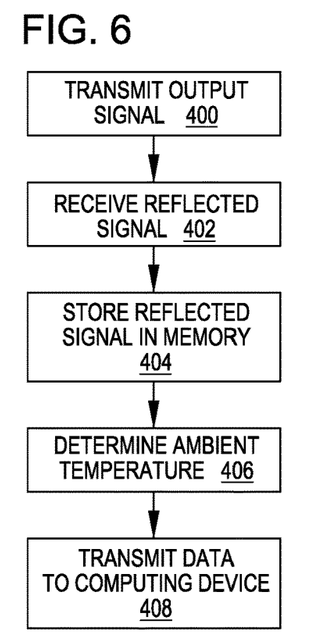
FIG. 6 shows a flow chart of a portion of a process for determining a characteristic of an insect using Doppler ultrasound using a system, according to an example of the present disclosure.

FIG. 6 is a flow chart of an exemplary process for determining various characteristics of an insect using Doppler ultrasound, for example, using the system 100, according to aspects of the present disclosure. The exemplary process is described with reference to the figures described herein, though other implementations are possible without departing from the scope of the present disclosure. In some examples, more or fewer steps of the described method may be performed by the system 100.

At block 400, the ultrasonic transceiver 108 can transmit an output signal 110 towards the interior of the tube 104 over a period of time. In some examples separate transmitters and receivers could be used in place of the ultrasonic transceiver 108. The ultrasonic transceiver 108 may transmit an output signal 110 having a frequency in the range of about 20,000 Hz to about 200,000 Hz over a period of time. The insect 106 (for example, the insect body and/or the insect wings) may reflect a portion of the output signal 110 back to the ultrasonic transceiver 108.

At block 402, the ultrasonic transceiver 108 may receive the reflected signal 114 over a period of time. The reflected signal 114 may have a frequency that is different from the frequency of the output signal 110. The difference between the frequency of the reflected signal 114 and the output signal 110 can correspond to the movement of the insect body and/or wings.

At block 404, the control unit 102 may store the reflected signal 114 in memory (e.g., memory 306 shown in FIG. 5). In some aspects, the control unit 102 may store a representation of the reflected signal 114 or a characteristic of the reflected signal 114, for example, but not limited to, the frequency of the reflected signal 114. The frequency can be determined using a Fourier transform. In some aspects, the reflected signal 114 may not be stored in memory, or may be stored elsewhere, including away from the control unit 102. For example, the memory may be random access memory (RAM), a memory card, a memory stick, cloud storage, or a network media.

At block 406, a temperature sensor, for example, additional sensor 304, may output a signal indicating the temperature near the insect 106. In some examples, additional sensors 304 may be included in the control unit 102 for determining additional environmental properties, for example, humidity. Temperature may affect the wing beat frequency of an insect. For example, the wing beat frequency of mosquitos can increase as the surrounding temperature increases.

At block 408, the control unit 102 may transmit data to the computing device 118. The data may include the output signal 110, the reflected signal 114, a representation of the output signal 110 and/or reflected signal 114, or a characteristic of the output signal 110 and/or the reflected signal 114 (e.g., a frequency or amplitude), the temperature data, and/or other additional data collected by additional sensors. In some examples, the control unit 102 may transmit data to cloud storage, network media, or other locations for signal and data processing. In some examples, the control unit 102 may not transmit data away from the control unit 102; in such examples the control unit 102 may include a processor that may process the reflected signal 114 and additional data (e.g., temperature data). The processor of the control unit 102 may access other networks, databases, and/or computing devices to store the data transmitted by the control unit 102. The processor of the control unit 102 may also access other networks, databases, and/or computing devices to process the data received from the control unit 102, for example, to perform a Fourier transform on a signal to determine the frequency of a signal, to filter a signal to extract certain components of the signal (e.g., components above or below a certain frequency), to determine the amplitude of a signal, or to perform other processing of a signal, including frequency domain processing.

Figure 7:
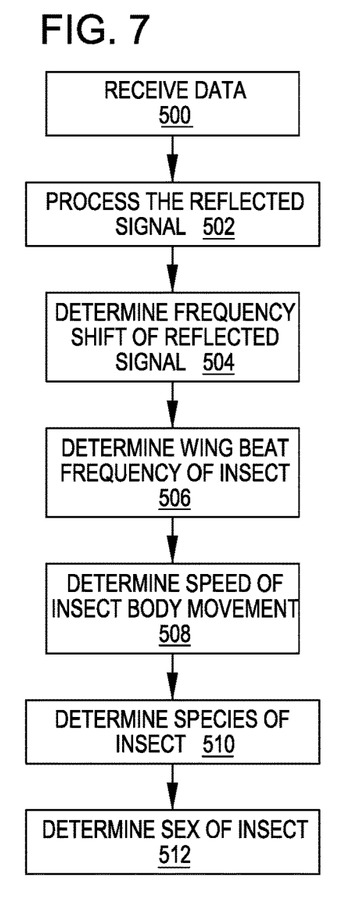
FIG. 7 shows a flow chart of a portion of a process for determining a characteristic of an insect using Doppler ultrasound using a system, according to an example of the present disclosure.

FIG. 7 is a flow chart of an exemplary process for determining various characteristics of an insect using Doppler ultrasound, for example, using the system 100, according to aspects of the present disclosure. The exemplary process is described with reference to the figures described herein, though other implementations are possible without departing from the scope of the present disclosure. In some examples, more or fewer steps of the described method may be performed by the system 100.

At block 500, the computing device 118 of the system 100 can receive data from the control unit 102, for example, as described in block 408 of FIG. 6. The data received from the control unit 102 can include, but is not limited to, the output signal 110, the reflected signal 114, a representation of the output signal 110 and/or the reflected signal 114, a characteristic of the output signal 110 and/or reflected signal 114 (e.g., a frequency of the output signal 110 and/or the reflected signal 114), temperature data, and/or other data gathered by additional sensors. In some examples, the output signal 110 may be a continuous-wave ultrasonic signal and reflected signal 114 may be a mixed signal that contains higher-frequency components and lower-frequency components. The higher-frequency components may be related to the relatively faster movement of the wings of the insect 106. The lower-frequency components may be related to the relatively slower motion of the body of the insect 106. The lower-frequency components may have a higher amplitude relative to the higher-frequency components, for example, due to the greater size of the body of the insect 106 as compared to the size of the wings of the insect 106.

At block 502, the computing device 118 may process the reflected signal 114. In some examples, the processor 308 of the computing device 118 may process the reflected signal 114. Processing the signal may include filtering or processing using converters. In some examples, to detect properties of the higher-frequency components, for example, to determine wing-beat frequency, an analog-to-digital converter with a high dynamic range may be used to sample the reflected signal 114. In place of, or in some examples, in addition to sampling the reflected signal 114 using the analog-to-digital converter, the reflected signal 114 may be applied to a high-pass or low-pass filter. For example, the reflected signal 114 can be applied to a low-pass filter to extract the lower-frequency components of the reflected signal 114 that relate to the movement of the body 205 of the insect 106 (e.g., to extract components below 150 Hz). In some examples, the reflected signal 114 can be applied to a high-pass or band-pass filter to extract higher-frequency components that relate to the movement of the wing 107 of the insect 106 (e.g., to extract components above 150 Hz). The extracted components may undergo additional processing by the system 100, for example, by the processor 308. In some examples, more or less processing and analysis of the reflected signal 114 and/or the output signal 110 may be performed by the system 100. In some examples, the frequency of the output signal 110 and the reflected signal 114 may be determined using a Fourier transform or frequency domain processing.

At block 504, the computing device 118 may determine the frequency shift or frequency change of the reflected signal 114 as compared to the output signal 110 over the period of time the reflected signal 114 was received. In other words, the computing device 118 may determine the Doppler shift of the reflected signal 114 from the output signal 110. The Doppler shift may be determined using Doppler shift equations, for example, where $f_{observed}$ is the frequency of the reflected signal 114 and v is the velocity of the output signal 110 (i.e., the speed of sound) and $v_{source}$ is the velocity of the insect body or insect wings, and $f_{source}$ is the frequency of the insect body or insect wings movement. The equations below can be used to solve for $v_{source}$.

Source receding: $f_{observed}=[v/v+v_{source}] f_{source}$

Source approaching: $f_{observed}=[v/v-v_{source}] f_{source}$

At block 506, the computing device 118 may determine the wing beat frequency of the insect 106. In some examples, the computing device 118 may determine the wing beat frequency of the insect 106 based on the change in frequency of the reflected signal 114 ($f_{source}$) and output signal 110 ($f_{observed}$). The computing device 118 may use the filtered components (e.g., portions of the signal extracted during filtering or processing) of the reflected signal 114 to determine the wing beat frequency of the insect 106. For example, the wing beat frequency could be determined by separating the high frequency portion of the reflected signal 114 from the low frequency portion of the reflected signal 114 using a high and low pass filter respectively. The high frequency portion of the reflected signal 114 can be related to the wing motion of the insect, and the low frequency portion of the reflected signal 114 can be related to the body motion of the insect. When the output signal 110 and the high frequency portion of the reflected signal 114 are multiplied, the resulting signal has a component at the difference frequency $f_{observed}-f_{source}$ and a component at the sum of $f_{observed}+f_{source}$. A low pass filter removes the sum component and leaves the difference component. The difference component can be the Doppler shift signal resulting from wing motion. The periodicity of that Doppler shift signal can be used to derive the wing beat frequency. The multiplication of the output signal 110 and the high frequency portion of the reflected signal 114 can be performed by hardware (e.g., by feeding both signals into a mixer circuit) or in software (e.g., software defined radio concepts). This is similar to demodulating FM radio signals. In some examples, the computing device 118 may use additional data in determining the wing beat frequency of the insect 106, including but not limited to, temperature data, time of day, and humidity data.

At block 508, the computing device 118 may determine the speed of the insect 106. In some examples, the computing device 118 may determine the speed of the insect 106 based on the change in frequency of the reflected signal 114 and output signal 110. For example, the computing device 118 may use the filtered components (e.g., portions of the signal extracted during filter or processing) to determine the speed of the insect 106. In some aspects additional information may be determined by the computing device, for example, the size of the insect. The computing device 118 may determine the size of the insect based on the output signal 110 and the reflected signal 114, for example, based on the amplitudes of the output signal 110 and the reflected signal 114. For example, the computing device 118 may use the filtered components (e.g., portions of the signal extracted during filtering or processing) of the reflected signal 114 to determine the speed of the insect 106. For example, the speed of the insect could be determined by separating the high frequency portion of the reflected signal 114 from the low frequency portion of the reflected signal 114 using a high and low pass filter respectively. The low frequency portion of the reflected signal 114 can be related to the body motion of the insect. The $v_{source}$ of the Doppler shift equation can be solved for, where $v_{source}$ is the speed of the insect, using the low frequency portion of the reflected signal 114 (the low frequency portion related to the $f_{observed}$). This is similar to the process described in block 506 for determining the wing beat frequency of the insect.

At block 510, the computing device 118 may determine the species of the insect 106. The computing device 118 may use classification algorithms (e.g., Bayesian classifier, k-Nearest Neighbor, Learning Vector Quantization, machine-learning, neural networks, signal processing, or other suitable processing means). The computing device 118 may determine the species of the insect 106 based on one or more of the wing beat frequency determined at block 506, the insect speed determined at block 508, the time of day, the temperature, the humidity, the age of the insect 106, and the size of the insect 106. In some examples, the computing device 118 may determine the species of the insect 106 based on data that includes, but is not limited to, an image of the insect 106 captured by a camera, data related to a measured distribution of insects in the area of the control unit 102, data related to the known wing beat frequency of various species of insects, the known size of various species of insects, the known speed of various species of insects, the known wing beat frequency of male and female insects of the same species, the known size of male and female species of insects, and/or the known speed of male and female insects of the same species.

At block 512, the computing device may determine the sex of the insect 106. For example, if the species of the insect is known, the computing device may compare the wing beat frequency of the insect to a list of known average ranges of wing beat frequencies for male and female insects of that species and may determine the sex of the insect based on which range of wing beat frequencies for male and females the measured wing beat frequency falls within. The computing device 118 may use classification algorithms (e.g., Bayesian classifier, k-Nearest Neighbor, Learning Vector Quantization, machine-learning, neural networks, signal processing, or other suitable processing means). The computing device 118 may determine the sex of the insect 106 based on one or more of the wing beat frequency determined at block 506, the insect speed determined at block 508, the insect species determined at block 510, the time of day, the temperature, the humidity, the age of the insect 106, and the size of the insect 106. In some examples the computing device 118 may determine the sex of the insect 106 based on data that includes but is not limited to, an image of the insect 106 captured by a camera, data related to a measured distribution of insects in the area of the control unit 102, data related to the known wing beat frequency of various species of insects, the known size of various species of insects, the known speed of various species of insects, the known wing beat frequency of male and female insects of the same species, the known size of male and female species of insects, and/or the known speed of male and female insects of the same species.

Operation of one example of the system 150 is illustrated in FIGS. 8-11. In the example shown in FIGS. 8-11, the sensor package 160 includes elements of a light curtain system 184 and a Doppler sensor system 186. The Doppler sensor system 186 may be an example of the Doppler sensor system 100 described above with respect to FIGS. 1A-7. However, the Doppler sensor system 186 is not limited to use of signals that are transmitted via sound waves. In some examples, the Doppler sensor system 186 may correspond to a laser Doppler system or other system that utilizes signals that are transmitted by light waves (e.g., outputting a laser or other light wave at one frequency, receiving a reflection at a different frequency, and using the difference in frequencies to determine a characteristic of an insect).

Broadly, the light curtain system 184 is utilized in determining the presence of one or more insects 180 in the test chamber 154, and this presence detection triggers activation of the Doppler sensor system 186 for use in determining one or more characteristics of the insect or insects 180 in the test chamber 154. Other components (including some described later) may additionally, or alternatively, be used in determining presence and/or characteristics of insects 180 in the test chamber 154.

In some arrangements, the Doppler sensor system 186 or other components may be used to detect both presence and characteristics. Nevertheless, using one set of components to detect presence and to accordingly trigger a separate set of components to detect characteristics may provide various benefits, such as reducing an amount of time that characteristic-detecting components are active and correspondingly reducing an amount of computational resources consumed and/or reducing an amount of extraneous collected data that might otherwise negatively affect the accuracy or precision of the characteristic-detecting components.

The light curtain system 184 may include a laser projector or other appropriate components for projecting light 188 across a cross-section of the test chamber 154. The light curtain system 184 can also include appropriate components for detecting changes to the projected light that result from an object passing through the cross-section. As one example, the light curtain system 184 may include a light sensor or receptor that outputs a first signal when receiving the projected light and outputs a second signal when the projected light is at least partially blocked from reaching the receptor (e.g., corresponding to an object blocking the projected light while passing through the cross-section). As another example, the light curtain system 184 may include a receptor for detecting a reflection of the projected light such that an amount of time between projecting the light and receiving the reflection can be determined. A change in the amount of time between light projection and reflection detection may indicate that an object has passed into the cross-section and caused the light to reflect sooner than would occur in the absence of an object being present in the cross-section.

Figure 8:
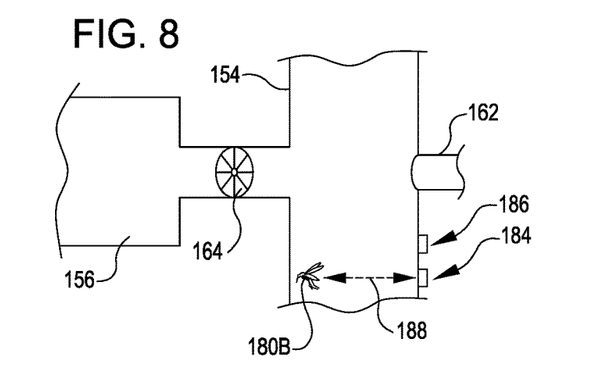
FIGS. 8-11 show an illustrative example of passage of insects during operation of one example of a portion of the system of FIG. 1.

Thus, referring to the illustrative example introduced in FIG. 8, a female mosquito 180B flying into the test chamber 154 (e.g., from the origination chamber 152 shown in FIG. 1) may affect light 188 projected by the light curtain system 184 in a manner that is detectable by the light curtain system 184. This detection may be communicated to the computer system 168 (e.g., via the communications link 170 shown in FIG. 1). In response, the computer system 168 may activate the Doppler sensor system 186 (e.g., via communications link 170 shown in FIG. 1).

Figure 9:
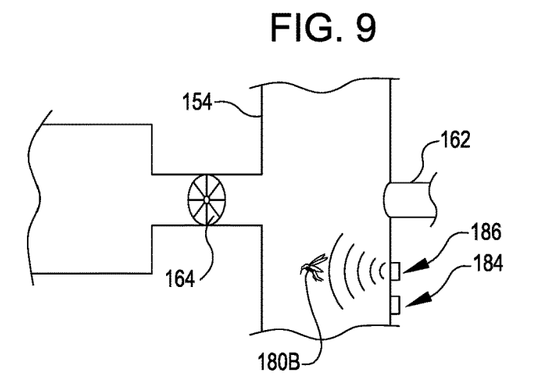

As shown in FIG. 9, the Doppler sensor system 186 may emit ultrasound waves into the test chamber and detect ultrasound waves reflected from the female mosquito. This may allow the Doppler sensor system 186 to detect information about the female mosquito 180B based on the reflected ultrasound waves and communicate at least a portion of that information to the computer system 168 (e.g., via communications link 170 of FIG. 1) for determination of characteristics of the female mosquito 180B (e.g., as described above with respect to FIGS. 1-7). As examples, the computer system 168 may process the information from the Doppler sensor system 186 to determine characteristics, such as wingbeat frequency and/or body movement speed of the female mosquito 180B. The computer system 168 may determine that the characteristics for the detected mosquito 180B fall within a threshold of stored reference values corresponding to female mosquitos. Based on this determination, the computer system 168 signal the air mover controller 174 to activate the air mover 162 for diverting the detected female mosquito.

Figure 10:
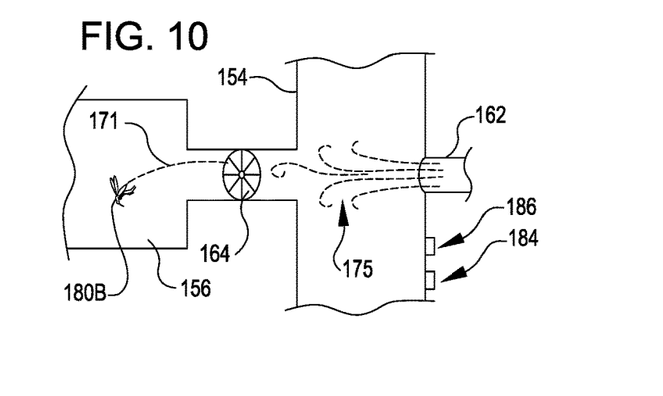

As shown in FIG. 10, activating the air mover controller 174 may provide a blast of air 175 into the test chamber 154 and drive the female mosquito 180B into the diverted chamber 156 (e.g., through the one-way valve 164 as illustrated by dashed line 171). The air mover controller 174 may be operated to cause the blast of air 175 to last for a suitable amount of time. For example, the air mover controller 174 may terminate the blast of air 175 after a certain duration and/or in response to a detection that the diverted chamber 156 has received the detected female mosquito 180B (e.g., which may be accomplished by including components similar to the laser curtain system 184 in the diverted chamber 156). Terminating the blast of air 175 may bring the system to a ready state for further detection of new insects in the test volume 154 (e.g., terminating the blast of air 175 may reduce an amount of airflow that may cause broadband noise that may otherwise interfere with readings from the Doppler sensor system 186).

Figure 11:
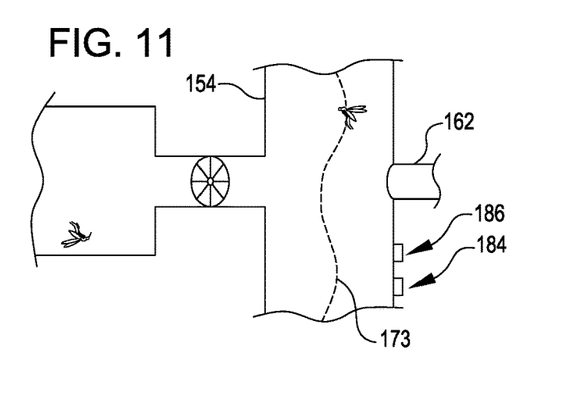

As shown in FIG. 11, a male mosquito 180A may elicit a different response. A male mosquito 180A flying into the test chamber 154 may affect light 188 projected by the light curtain system 184 and correspondingly trigger activation of the Doppler sensor system 186 for obtaining information about the male mosquito 180A (e.g., similar to the progression shown for the female mosquito 180B in FIGS. 8-9). The computer system 168 may determine that the characteristics for the detected mosquito 180A fall within a threshold of stored reference values corresponding to male mosquitos. Based on this determination, the computer system 168 may control the air mover controller 174 for the air mover 162 (e.g., causing it to deactivate or remain inactive to prevent it from providing diverting airflow). This may permit the male mosquito 180A to continue flying out of the test chamber 158 and toward the pass-through chamber 158 (e.g., as illustrated by the dashed line 173).

As a result of the example operation shown in FIGS. 8-11, male mosquitos 180A and female mosquitos 180B may be respectively separated into the pass-through chamber 178 and the diverted chamber 156. This arrangement may permit male mosquitos 180A to be collected without subjecting them to the blast of air pressure used to push female mosquitos 180B into the diverted chamber 156. Indeed, this may contrast with some known techniques that eliminate female mosquitos in a batch by exposing the whole batch to harsh temperatures, radiation, or other conditions that cannot be survived by female mosquitos but that can be survived by male mosquitos. The presently described arrangement (e.g., shown in FIGS. 8-11) may instead permit male mosquitos 180A to be collected without subjecting them to harsh female-mosquito-eliminating conditions that may otherwise risk damage to the male mosquitos 180A.

While the above describes male mosquitos 180A being directed into the pass-through chamber 178 and female mosquitos 180B being directed into the diverted chamber 156, other arrangements are possible. For example, a configuration of the arrangement could be reversed such that female mosquitos 180B are directed into the pass-through chamber 178 and male mosquitos 180A are directed into the diverted chamber 156. Additionally, criteria corresponding to characteristics other than male or female sex or gender could be used as the basis for separating insects. Examples may include, but are not limited to, separating insects based on size (e.g., such that insects under a particular size are diverted), activity (e.g., such that insects moving under a certain speed are diverted) or species (e.g., such that insects of particular species are diverted while other species are permitted to continue through). Moreover, although the system 150 is shown with a single test chamber 154, in some examples, more than one test chamber 154 may be included, for example, to provide redundancy for detecting and eliminating any female mosquitos 180B in case any manage to pass through a first test chamber 154 undetected.

Figure 12:
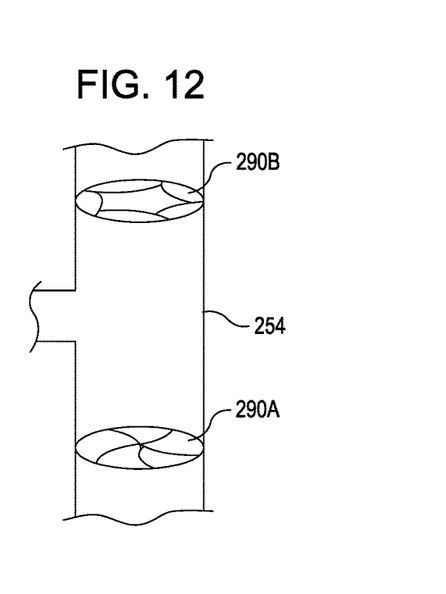
FIG. 12 shows an illustrative example of closures that may be used in the system of FIG. 1.

FIG. 12 illustrates another chamber 254 having features that may be additionally, or alternatively, used in the system 150. The chamber 254 shown in FIG. 8 includes closures 290 (individually shown in FIG. 8 as an entry closure 290A in a closed configuration and an exit closure 290B in an open configuration). The closures 290 are shown as orifices that can be open or shut by collectively rotating overlapping curved panels toward or away from the center of the area, but may correspond to any structure capable of selectively blocking and allowing access through an area. Other examples include, but are not limited to, actuatable flaps or linearly sliding plates.

The closures 290 may be controlled by the computer system 268 (e.g., via the communications link 170 introduced in FIG. 1). The entry closure 290A may be used to regulate entry of mosquitos 280 into the chamber 254, and the exit closure 290B may be used to regulate exit of mosquitos 280 from the chamber 254. For example, the entry closure 290A may be closed to limit a number of mosquitos 280 in the chamber 254. Additionally, or alternatively, the entry closure 290A may be closed to prevent a mosquito 280 from returning to the origination chamber 252 before adequate information about the mosquito 180 can be obtained from the sensor package 260 for determining where to direct the mosquito 180. Similarly, the exit closure 290B may be closed to prevent a mosquito 280 from moving out of the chamber 254 before adequate information about the mosquito 180 can be obtained from the sensor package 260 for determining where to direct the mosquito 180. Additionally, or alternatively, the exit closure 290B may be closed to prevent inadvertent diversion of mosquitos 180 that have already been permitted to exit the chamber 254 without diversion. In some aspects, the closures 290 may act as noise barriers that may diminish transmission of sound or other signals that may interfere with or otherwise adversely affect readings from the sensor package 260.

In some aspects, the closures 290B may be operated based on detection systems that may be similar to and/or include the light curtain system 184 shown in FIGS. 8-11. For example, where FIGS. 8-11 show a light curtain system 184 near an entry to the test chamber 154, similar components may be additionally, or alternatively, included near any entry and/or exit of the test chamber 254 in FIG. 10 to facilitate detection of entry and/or exit of insects from the test chamber 254 (e.g., so that the closures 290 may be controlled in response to detected insect entry and/or exit to permit new insects into the test chamber 254 when it has been detected that insects previously in the test chamber 254 have been successfully moved out of the test chamber 254).

Figure 13:
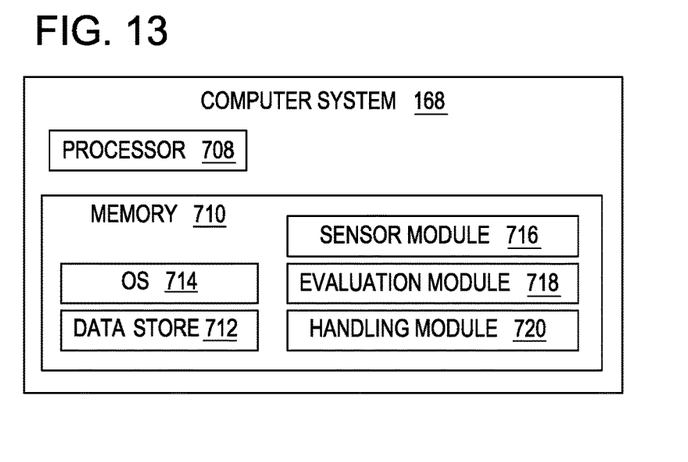
FIG. 13 is a block diagram illustrating an example of a computer system that may be used in the system of FIG. 1.

FIG. 13 is a block diagram illustrating an example of the computer system 168 of the system 150. The computer system 168 may include less or more than the elements shown. For example, the computer system 168 may additionally, or alternatively, include elements of the computer system 118 described with reference to respect to FIG. 5. The computer system 168 illustrated in FIG. 9 includes a processor 708 and memory 710.

The processor 708 may be implemented as appropriate in hardware, computer-executable instructions, firmware, or combinations thereof. Computer-executable instruction or firmware implementations of the processor 708 may include computer-executable or machine-executable instructions written in any suitable programming language to perform the various functions described.

Turning to the contents of the memory 710 in more detail, the memory 710 may include an operating system 714, one or more data stores 712 and/or one or more application programs, services, or other software modules, which are generally executed by the processor 708 for implementing the features disclosed herein. Example modules are shown in FIG. 9, but functions and examples described herein can utilize a subset of the features provided by the modules and/or additional functions can be provided. As example, modules of memory 710, a sensor module 716, an evaluation module 718, and a handling module 720 can be provided.

The sensor module 716 can interact with the sensor package 160 of the system 150, such as by receiving information from the sensor package 160 and/or providing instructions to activate or deactivate elements of the sensor package 160. The sensor module 716 may interact with presence sensor elements (such as those of the light curtain system 184) and/or characteristic sensor elements (such as those of the ultrasonic Doppler sensor system 186 or other characteristic sensor systems). In some examples, the sensor module 716 may additionally, or alternatively, interact with characteristic sensor elements corresponding to laser Doppler sensors, optical sensors, or other sensors capable of obtaining information that can be utilized to determine characteristics of insects in the test chamber 154.

The evaluation module 718 can evaluate information received from the sensor 160. This may include processing sensor information to determine characteristics of an insect in the test chamber 154. In some examples, the evaluation module 718 may process information from ultrasonic or laser Doppler sensors to determine wing beat frequency or body movement information of one or more insects in the test chamber 154. This information may be indicative of whether any insects in the test chamber 154 are female mosquitos, for example. In some examples, the evaluation module 718 may additionally, or alternatively, process information from an optical sensor or other image capture device and perform image recognition processes to identify physiological features corresponding to criteria of interest, such as whether the identified physiological features correspond to male or female insects. Shape, color, presence, size, and/or other factors associated with physiological features may provide suitable distinguishing criteria. Examples of physiological features that may be considered include, but are not limited to, antennae, body segments, wings, and/or any other characteristics that may be identified by application of neural network or other machine learning techniques or other forms of vision tools (such as a blob finder, an edge detector, etc.). In some aspects, machine-learning models may be trained to recognize specific features (which may include those listed above) and/or trained by introduction of images categorized according to criteria of interest, such as images of male mosquitos and images of female mosquitos.

The evaluation module 718 may determine how the test chamber 154 should be handled based on the determined characteristics. As an illustrative example, the evaluation module 718 may determine that the test chamber 154 warrants evacuation based on a detected wingbeat frequency that is below a wingbeat frequency associated with a male mosquito. More broadly, the evaluation module 718 may determine that an insect in the test chamber has a certain characteristic defined with any suitable level of generality or specificity. For example, the evaluation module 718 may determine a generalized characteristic, such as "female" or may determine a particularized characteristic, such as having a wingbeat frequency falling within a range associated with female mosquitos in a particular set of data. Based on the characteristic determined, the evaluation module 718 may select a response accordingly.

The handling module 720 may provide suitable instructions for handling the contents of the chamber 154. For example, with respect to the arrangement shown in FIG. 1, the handling module 720 may provide instructions that cause or prevent activation of the air mover controller 174. In some examples, the handling module 720 may provide instructions to cause opening or closure of particular closures 190. In some examples, the handling module 720 may deactivate the characteristic sensor, for example, during evacuation or handling of the chamber 154 or to reset for the next time the presence sensor warrants triggering the characteristic sensor.

Figure 14:
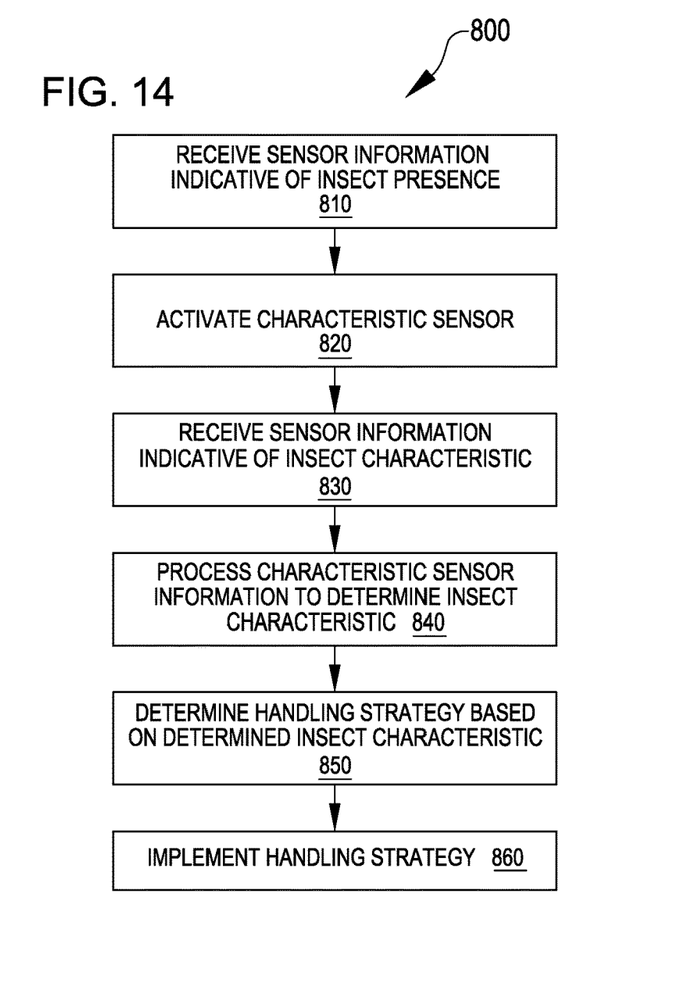
FIG. 14 is a flowchart illustrating a process that may be performed by the computer system of FIG. 13.

FIG. 14 is a flowchart illustrating a process 800 that may be performed by the computer system 168. The process 800 will also be described with reference to other elements of the system 150 introduced in FIG. 1 by way of example.

The process 800 at 810 may include receiving sensor information indicative of the presence of an insect in the chamber. In one example, this may include the sensor module 716 receiving information from the light curtain system 184. For example, a laser receiver of the light curtain system 184 may detect a change in laser light emitted from a laser emitter (e.g., due to an insect flying into the laser light as in FIG. 8) and register an increase or drop in voltage (or other relevant signal) that is communicated to the computer 168. In another example, the Doppler system 186 may register a reflected light or sound signal from the chamber 154 at a different frequency than was emitted (e.g., indicating movement of an insect in range of the Doppler system 186), and this information may be relayed to the computer 168 for the sensor module 716 to register that an insect's presence has been detected.

The process 800 at 820 may include providing instructions for activating a characteristic sensor. This may include the sensor module 716 communicating commands to elements of the Doppler sensor system 186, optical sensors, or any other forms of sensors described herein. For example, the sensor module 716 of the computer 168 may respond to the indication of insect presence from 810 by providing signals for a transceiver 108 to begin emitting output frequencies and/or to begin registering reflection frequencies. As another example, the sensor module 716 may trigger an optical sensor (if present in the sensor package 160) to begin taking images of insects in the test chamber 154.

The process 800 at 830 may include receiving sensor information indicative of characteristics of an insect in the chamber. This may include the sensor module 716 receiving data from elements of the Doppler sensor system 186, optical sensors, or any other forms of sensors described herein. For example, the sensor module 716 may receive magnitudes of the output signal 110 and the reflected signal 114 from the transceiver 108. Further, the sensor module 716 may receive temperature and/or humidity data from temperature and/or humidity sensors if present in the sensor package 160. As another example, the sensor module 716 may receive insect images obtained by the optical sensor (if present in the sensor package 160).

The process 800 at 840 may include processing the characteristic sensor information to determine a characteristic of the insect in the chamber. For example, this may include the evaluation module 718 processing data received by the sensor module 716 at 830 from elements of the Doppler sensor system 186, optical sensors, or any other forms of sensors described herein to determine a characteristic of a detected insect. For example, the evaluation module 718 may compare relevant frequencies of output and reflection signals from the transceiver 108 to determine Doppler shifts and corresponding characteristics, such as species, size, sex, etc., of insects in the test chamber 154. The evaluation module 718 may use humidity and temperature information received at 830 to determine a speed of sound or other relevant information for improving accuracy of the Doppler shift calculations or other analysis. The evaluation module 718 may perform image recognition techniques on images received at 830 to improve a confidence of characteristics determined based on Doppler shift information or as a substitute for such Doppler shift-based characteristic determination.

The process 800 at 850 may include determining a handling strategy based on the determined characteristics. For example, this may include the evaluation module 718 comparing the characteristics determined at 840 against criteria (e.g., against a stored threshold value or a stored range) and determining a handling strategy based on that comparison. For example, a handling strategy of non-interference may be determined based on a characteristic matching one set of criteria (e.g., a calculated wingbeat frequency corresponding to stored values for male mosquitos of a certain species), or a handling strategy of elimination may be determined based on a characteristic matching other criteria (e.g., a calculated wingbeat frequency corresponding to stored values for female mosquitos of a certain species). Moreover, although the system 150 introduced in FIG. 1 is primarily described herein with an eliminating strategy that corresponds to use of an airflow system to move an insect into a diverted chamber 156, other elimination strategies may be utilized, including, but not limited to, use of electric arcs to kill insects (e.g., in the test volume).

The process 800 at 860 may include providing instructions for implementing the determined handling strategy. For example, this may include the handling module 720 providing instructions to the air mover controller 174 of FIG. 1, to cause the air mover 162 to blast the insects out of the test chamber 154 (e.g., based on the evaluation module 718 at 850 determining that diverting is an appropriate handling strategy for the detected mosquitos with female characteristics). Alternatively, this may include the handling module 720 providing instructions to the air mover controller 174 to prevent the air mover 162 from blasting the insects out of the chamber (e.g., based on the evaluation module 718 at 850 determining that non-interference is an appropriate handling strategy for the detected mosquitos with only male characteristics). In other examples, the handling module 720 at 860 could provide activation signals to an electrical element to eliminate female mosquitos in the test chamber 154 and/or in the diverted chamber 156.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure. For example, more or fewer steps of the processes described herein may be performed according to the present disclosure. Moreover, other structures may perform one or more steps of the processes described herein.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Some examples in this disclosure may include a processor. A computer-readable medium, such as RAM may be coupled to the processor. The processor can execute computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices, such as programmable logic controllers (PLCs), programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example, computer-readable storage media, that may store instructions that, when executed by the processor, can cause the processor to perform the steps described herein as carried out, or assisted, by a processor. Examples of computer-readable media may include, but are not limited to a memory chip, ROM, RAM, ASIC, or any other medium from which a computer processor can read or write information. The processor, and the processing described, may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

That which is claimed is:

1. An insect separating apparatus comprising:
   a first receptacle sized for insect receiving;
   a test chamber defining a test volume;
   a first enclosed path connecting the test volume to the first receptacle;
   an optical sensor positioned relative to the test volume for obtaining sensor information about an insect received in the test volume;
   an air mover selectively operable to apply suction or provide pressurized air to move air toward the first enclosed path in response to an activation signal; and
   a computing device comprising a processor and a non-transitory computer-readable medium comprising processor-executable instructions to cause the processor to:
      receive sensor information from the optical sensor;
      determine whether the received sensor information is indicative of at least one female insect being present in the test volume; and
      cause the activation signal to be sent to the air mover to apply suction or provide pressurized air in response to the received sensor information being indicative of at least one female insect being present in the test volume.

2. The insect separating apparatus of claim 1, wherein the processor-executable instructions further cause the processor to send a signal to the air mover for preventing the air mover from moving air toward the first enclosed path and in response to the received sensor information being indicative of one or more insects being present in the test volume that do not include at least one female insect.

3. The insect separating apparatus of claim 2, further comprising a one-way valve arranged in the first enclosed path and configured to:
   permit passage of contents from the test volume into the first receptacle in response to air being blown by the air mover toward the first receptacle; and
   prevent passage of contents from the first receptacle into the test volume.

4. The insect separating apparatus of claim 1, wherein the air mover is selectively operable to apply suction.

5. The insect separating apparatus of claim 1, further comprising an origination chamber coupled with the test volume so as to allow insect flight from the origination chamber into the test volume.

6. The insect separating apparatus of claim 1, further comprising a laser curtain system comprising a laser emitter and a laser receiver, wherein the sensor is configured to obtain sensor information in response to the laser curtain system detecting one or more insects passing a threshold position.

7. A method comprising:
   receiving image sensor information from a camera about an insect located within a chamber;
   determining a characteristic of the insect based at least in part on the image sensor information; and
   selectively activating an air mover to apply suction or provide pressurized air to remove the insect from the chamber based on the characteristic determined being indicative of the insect being female.

8. The method of claim 7, wherein selectively activating the air mover based on the characteristic determined comprises activating the air mover in response to the characteristic matching stored criteria corresponding to a female mosquito.

9. The method of claim 7, wherein selectively activating the air mover based on the characteristic determined comprises deactivating the air mover or maintaining the air mover in a deactivated condition in response to the characteristic matching stored criteria corresponding to a male insect.

10. The method of claim 8, wherein selectively activating the air mover based on the characteristic determined comprises deactivating the air mover or maintaining the air mover in a deactivated condition in response to the characteristic matching stored criteria corresponding to the absence of a female mosquito.

11. The method of claim 7, wherein the characteristic of the insect comprises a wing beat frequency of the insect.

12. The method of claim 7, wherein the characteristic of the insect comprises a speed of the insect, an acceleration of the insect, and/or a flight path change of the insect.

13. The method of claim 7, wherein the characteristic of the insect comprises a size of the insect.

14. The method of claim 7, wherein the characteristic of the insect comprises a species of the insect.

15. The method of claim 7, wherein the insect is a mosquito.

16. A system comprising:
   a sensor positioned relative to a chamber for obtaining visual sensor information about an insect received in the chamber; and
   a separator selectively operable to facilitate movement of the insect from the chamber toward a first exit of the chamber in response to the visual sensor information being indicative of the insect matching certain criteria corresponding to the insect being female.

17. The system of claim 16, wherein the sensor comprises an optical sensor and the visual sensor information comprises image information relative to the insect received in the chamber, and wherein the visual sensor information being indicative of the insect matching or not matching the certain criteria is based at least in part on performance of image recognition techniques on the image information.

18. The system of claim 16, wherein the separator comprises an air mover.

19. The system of claim 16, wherein the separator comprises at least one selectively operable closure.

* * * * *